United States Patent [19]  [11] Patent Number: 5,399,779
Tortelli et al.  [45] Date of Patent: Mar. 21, 1995

[54] PROCESS FOR PREPARING PERFLUORO-2-METHYL-4-METHOXYPENTANE

[75] Inventors: Vito Tortelli, Milan; Claudio Tonelli, Concorezzo; Walter Navarrini, Boffalora Ticino; Simonetta Fontana, Milan, all of Italy

[73] Assignee: Ausimont S.p.A., Milan, Italy

[21] Appl. No.: 121,757

[22] Filed: Sep. 15, 1993

[30] Foreign Application Priority Data

Sep. 24, 1992 [IT] Italy ............... MI92A2181

[51] Int. Cl.⁶ .............................. C07C 41/06
[52] U.S. Cl. ..................................... 568/685
[58] Field of Search ........................ 568/683

[56] References Cited

U.S. PATENT DOCUMENTS 4,577,044  3/1986  Campbell et al. ............ 568/683
5,292,961  3/1994  Marraccini et al. ........... 568/604

FOREIGN PATENT DOCUMENTS 0404076  12/1990  European Pat. Off. .

OTHER PUBLICATIONS

European Search Report dated Dec. 23, 1993 for EP 93 11 5069.

Primary Examiner—Howard T. Mars
Attorney, Agent, or Firm—Bryan Cave

[57] ABSTRACT

Perfluoro-2-methyl-4-methoxypentane is prepared with high selectivity by reacting perfluoro-4-methyl-2-pentene with $CF_3OF$ at a temperature ranging from $-40°$ to $+50°$. The reaction is preferably carried out by continuously bubbling a gaseous $CF_3OF$ flow into a liquid phase consisting of the abovesaid pentene optionally dissolved in a solvent.

5 Claims, No Drawings

PROCESS FOR PREPARING PERFLUORO-2-METHYL-4-METHOXYPENTANE

The present invention relates to a process for preparing perfluoro-2-methyl-4-methoxypentane

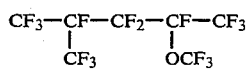

(I)

It is known that for the electronic testing use is made of low molecular weight perfluoropolyethers produced by Ausimont S.p.A., sold under the trademark Galden®.

Such perfluoropolyethers have the following formula

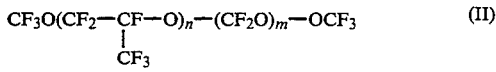

(II)

wherein the n/m ratio is usually equal to 40.

These products are obtained by means of oxypolymerization of perfluoropropene.

Their high performances in the electronic testing originate in the following combination of properties: high chemical and thermal stability, high difference between pour point and boiling temperature, perfect compatibility with the materials utilized in electronics, low viscosity also at low temperature and absence of toxicity.

The great difference between pour point and boiling temperature and the low viscosity of these products originate in the presence of ethereal oxygen atoms in the molecules.

Since the preparation of Galden is based on a sequence of often complex chemical reactions, it would be convenient to have available a simple process capable of providing products having similar characteristics.

A process that, at first sight, would allow the preparation of perfluoroalkoxy perfluoroalkanes, i.e. compounds having structure similar to the one of the perfluoropolyethers, is based on the reaction of a perfluorinated alkene with a perfluoroalkyl hypofluorite according to the scheme:

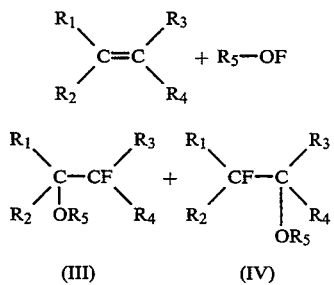

However, it is well known that the addition of a perfluoroalkyl hypofluorite to a non symmetric olefin gives rise to the formation of the two regioisomers (III) and (IV): see for example K.K. Johri et al., Journal of Organic Chemistry, 1983, 48, 242–250.

Since in the electronic testing it is highly desirable that the testing fluid should exhibit constant chemical physical characteristics for all the duration of the test, the use of a mixture of compounds is undesirable.

It has now surprisingly been found that if a particular asymmetric perfluoropolyolefin and a particular perfuoroalkyl hypofluorite are used in the abovesaid reaction, the reaction occurs with a very high regioselectivity and a very high yield, wherefore a practically pure perfluoroalkoxyperfluoroalkane (the perfluoro-2-methyl-4-methoxypentane) is obtained.

Thus, it is an object of the present invention to provide process for preparing perfluoro-2-methyl-4-methoxypentane at a high purity degree.

Another object is to provide a process which permits to obtain the abovesaid product with a very high yield starting from easily available starting materials.

These and still further objects are achieved by the process of the present invention for the preparation of perfluoro -2-methyl-4-methoxypentane having a regioselectivity of at least 94%. This process is characterized in that perfluoro-4-methyl-2-pentene (dimer of perfluoropropene)

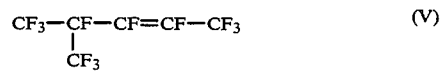

(V)

is reacted with perfluoromethyl hypofluorite $CF_3OF$ at a temperature ranging from $-40°$ to $+50°$. Preferably, the temperature ranges from $0°$ to $+30°$ C.

The reaction is preferably conducted according to the following procedure: a $CF_3OF$ gas flow is continuously bubbled into a liquid phase consisting of perfluoro-4-methyl-2-pentene optionally dissolved in a solvent which is inert under the reaction conditions.

The gaseous $CF_3OF$ can be diluted in an inert gas, for example $N_2$ or He. In such case, the inert gas/$CF_3OF$ volume ratio generally ranges from 0.5 to 10 and, more usually, from 0.5 to 3.

Although it is possible to operate in the absence of an inert gas for the whole duration of the reaction, $CF_3OF$ can be diluted only at the beginning of the reaction, and then it can be used in the undiluted state: this procedure increases the reaction rate. In other terms, it is possible to dilute $CF_3OF$ until about 2–10% of perfluoro-4-methyl-2-pentene has reacted, and then it can be utilized in the undiluted state.

The solvent, if any, can be for example a chlorofluorocarbon such as, for example, $CFCl_2$—$CF_2Cl$ or a perfluoropolyether, such as e.g. a Fomblin ®Y produced by Ausimont.

Generally, a $CF_3OF$ flowrate ranging from 1 Nl/h to 15 Nl/h is used for each mole of perfluoro-4-methyl-2-pentene in the liquid phase.

The reaction can be also conducted batchwise, as illustrated in example 3; however, on a commercial scale, it is generally preferred to operate semicontinuously by feeding a gaseous $CF_3OF$ flow into the perfluoro-4-methyl-2-pentene in the liquid phase, as described before.

The reaction products are:

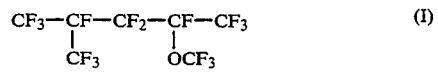

(I)

along with small amounts of its regioisomer:

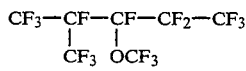

and with small amounts of perfluoroalkane

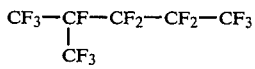

The reaction regioselectivity, calculated as the ratio between the amount of compound (I) and the total amount of compounds (I) and (VI) is at least of about 94% and, more generally, of at least 95%.

Generally, the olefin conversion is quantitative.

At the end of the reaction, the unreacted $CF_3OF$ is removed. To this purpose—when it is operated semi-continuously—an inert gas stream is made to flow in the reactor in order to strip the unreacted $CF_3OF$ contained in the liquid phase.

The reaction products (I) and (VI) are then separated from the solvent, if any, and, usually, also from perfluoroalkane (VII) by means of distillation.

As already explained, perfluoro-2-methyl-4-methoxy-pentane is suitable as a fluid for the electronic testing. In such application it is particularly suitable to be used as a cooling fluid and as a heat transfer fluid. Favourable characteristics of the product in this connection are a fairly high boiling point (85° C.) and a low pour point (less than −100° C., according to ASTM D 97-66, NOM 30-71).

The starting products utilized in the process of the present invention are easily available. The perfluoro-4-methyl-2-pentene is the well-known dimer of the perfluoropropene. As known, it can be prepared via anionic dimerization of perfluoropropene.

$CF_3OF$ can be prepared, for example, according to the process described by G. H. Cady and K. B. Kellogg in J. Am. Chem. Soc. 70, 3986, 1948.

The following examples are given to better illustrate the present invention and are not to be construed as limitative of the scope thereof.

EXAMPLE 1

A 100 ml glass reactor was used equipped with mechanical stirrer, thermometer, cooler to −78° C. and gas feeding pipe reaching the reactor bottom.

The reactor was fed with 30.4 g (0.1 mole) of perfluoro-4-methyl-2-pentene and 85 g of a solvent consisting of perfluoropolyether Fomblin®Y VAC 06/6 of formula:

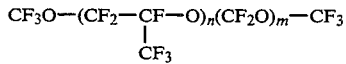

wherein the n/m ratio is equal to about 25 and the number average molecular weight is of about 1,800.

Then, while the internal temperature of the reactor was maintained at +30° C., a gaseous flow of 1 Nl/h of $CF_3OF$ and 0.5 Nl/h of $N_2$ was initially bubbled into the liquid phase; bubbling was continued for one hour; subsequently the $N_2$ flow was eliminated and 1 Nl/h of $CF_3OF$ was fed for further three hours. At the end of the reaction, a He flow (1 Nl/h) was bubbled at room temperature for one hour in order to strip the unreacted $CF_3OF$ contained in the solution.

After stripping under vacuum, 36.8 g of products were obtained from the rough reaction product; the composition of the mixture of the reaction products, determined by gas chromatography and $^{19}F$ NMR was as follows:

compound (I) 94% (by weight)
compound (VI) 4%
compound (VII) 2%.

The regioselectivity, determined as illustrated above, was equal to 96%.

Olefin conversion: 100%.

The perfluoroalkane (VII) was separated by fractionated distillation.

EXAMPLE 2

Into the same reactor of example 1 77.6 g (0.26 mole) of perfluoro-4-methyl-2-pentene were charged; no solvent was added.

While maintaining the temperature of the liquid phase at +30° C., a flow of 0.7 Nl/h of $CF_3OF$ and 0.5 Nl/h of $N_2$ was fed for one hour and, thereafter, a flow of 1.5 Nl/h of $CF_3OF$ was fed for 4.5 hours.

On conclusion of the reaction, a He stream was made to flow in the same manner as explained in example 1. 100 g of products were obtained; the composition of the mixture of the reaction products, determined by means of the same methods of analysis as indicated in example 1, was the following:

compound (I) 95%
compound (VI) 3.5%
compound (VII) 1,5%
Regioselectivity: 96.5%
Olefin conversion: 100%.

Perfluoroalkane (VII) was separated by fractionated distillation.

EXAMPLE 3

This example describes a batch reaction. In a glass reactor there were condensed, by means of a vacuum line, 1 g (0.0033 moles) of perfluoro-4-methyl-2-pentene and 3 ml of $CFCl_3$. Subsequently 0.62 g (0.006 moles) of $CF_3OF$ were also condensed in the reactor.

The reactor temperature was allowed to reach 25° C. in about 15 hours and the reactor was maintained at this temperature for further 15 hours. Then, a trap-to-trap-distillation was carried out and the $CF_3OF$ in excess was removed in a trap at −196° C.

The mixture of reaction products was then analyzed by means of gas chromatography and $^{19}F$ NMR.

The following products were obtained:
product (I) 90%
product (VI) 5%
product (VII) 5%
Regioselectivity: 94.7%
Olefin conversion: 100%.

EXAMPLE 4 (COMPARATIVE)

It was operated batchwise under identical conditions to those of example 3, with the exception of the conditions which are specifically indicated, using an asymmetric perfluoromonoolefin different from perfluoro-4-methyl-2-pentene.

1 g (0.0033) moles of $(CF_3)_2C=CF—CF_2—CF_3$, 3 ml of $CFCl_3$ and 0,62 g (0,006 moles) of $CF_3OF$ were condensed in the reactor.

The reactor temperature was allowed to reach 25° C. in about 15 hours and the reactor was maintained at this temperature for further 15 hours. CF$_3$OF in excess was then removed in the same manner as in example 3.

The mixture of reaction products was analyzed by gas chromatography and $^{19}$F NMR.

The following products were obtained:

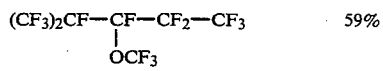   59%   (VIII)

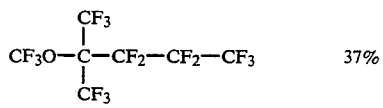   37%   (IX)

   4%   (X)

The regioselectivity of compound (VIII) was only of 61%. The olefin conversion was of 62%.

It is claimed:

1. A process for preparing perfluoro-2-methyl-4-methoxypentane with a regioselectivity of at least 94%, wherein perfluoro-4-methyl-2-pentene is reacted with perfluoromethyl hypofluorite at a temperature ranging from −40° to 50° C.

2. The process of claim 1, wherein the temperature ranges from 0° to +30° C.

3. The process of claim 1, wherein a gaseous flow of perfluoromethyl hypofluorite is continuously bubbled into a liquid phase comprising perfluoro-4-methyl-2-pentene optionally dissolved in a solvent which is inert under the reaction conditions.

4. The process of claim 3, wherein, at the beginning of the reaction, the CF$_3$OF flow is diluted with an inert gas.

5. The process of claim 3 wherein the solvent is selected from the group consisting of chlorofluorocarbons and perfluoropolyethers.

* * * * *